United States Patent [19]

Sakurada

[11] 4,315,891
[45] Feb. 16, 1982

[54] AUTOMATIC ANALYTICAL APPARATUS
[75] Inventor: Masahiko Sakurada, Machida, Japan
[73] Assignee: Olympus Optical Co. Ltd., Tokyo, Japan
[21] Appl. No.: 140,795
[22] Filed: Apr. 16, 1980
[30] Foreign Application Priority Data
  Apr. 28, 1979 [JP] Japan ................................. 54-52895
[51] Int. Cl.³ ...................... G01N 35/04; G01N 35/06
[52] U.S. Cl. ........................................ 422/64; 422/65; 356/222
[58] Field of Search ............................ 422/64, 65, 67; 356/222

[56] References Cited
U.S. PATENT DOCUMENTS
3,716,338 2/1973 Moran ................................... 422/65
3,832,135 8/1974 Drozdowski et al. ................ 422/65
3,883,303 5/1975 Hoskins et al. ...................... 422/65

Primary Examiner—Ronald Serwin
Attorney, Agent, or Firm—Stevens, Davis, Miller & Mosher

[57] ABSTRACT

An automatic analytical apparatus which comprises a single reaction line and in which reaction vessels are carried step by step along the reaction line, a sample and reagent are delivered to the reaction vessel during each carrying step to obtain a test liquid, and the test liquid thus obtained is subjected to a photometric operation, characterized by comprising (a) sample and reagent delivering means for delivering the sample and reagent into a plurality of reaction vessels in succession, respectively, during each carrying step of the reaction vessel, and (b) means for subjecting the photometric operation to a plurality of test liquids at separate positions at the same time during each carrying step of the reaction vessel.

4 Claims, 3 Drawing Figures

AUTOMATIC ANALYTICAL APPARATUS

BACKGROUND OF THE INVENTION

1. Field of the Invention

This invention relates to an automatic analytical apparatus which comprises a single reaction line and in which reaction vessels are carried step by step along the reaction line, a sample and reagent are delivered to the reaction vessel during each carrying step to obtain a test liquid, and the test liquid thus obtained is subjected to a photometric operation.

2. Description of the Prior Art

In the above described type of automatic analytical apparatus, that is, in a so-called single line multitest automatic analytical apparatus, heretofore it has been the common practice to effect the sample or reagent delivering step by spending time which is the same as the time spent when the test liquid is subjected to the photometric operation. The reaction vessels were carried one by one on the basis of the time required for the photometric operation. As a result, if the interval between the successive carrying steps is made short for the purpose of improving the treating ability of the apparatus, it is indispensable to shorten the photometric operation time, thereby degrading the analytical precision. Under such circumstances, it has heretofore been considered that on the order of 120 test bodies only can be analyzed per 1 hour. But, such treating ability can not sufficiently satisfy the requirement for the testing chamber which makes use of the automatic analytical apparatus.

SUMMARY OF THE INVENTION

An object of the invention, therefore, is to provide a single line multitest type automatic analytical apparatus which does not need to shorten the photometric operation time and hence can improve the treating ability.

A feature of the invention is the provision of an automatic analytical apparatus comprising a single reaction line, reaction vessels arranged along the reaction line and operative to be carried step by step, a sample delivering station for delivering a sample to the reaction vessel during each carrying step thereof, a reagent delivering station for delivering a reagent corresponding to the measurement item to the reaction vessel to obtain a test liquid during each carrying step thereof and a photometric station for subjecting the photometric operation to the test liquid thus obtained, characterized by comprising (a) sample and reagent delivering means for delivering the sample and reagent into a plurality of reaction vessels in succession, respectively, during each carrying step of the reaction vessel, and
(b) means for subjecting the photometric operation to a plurality of test liquids at separate positions at the same time during each carrying step of the reaction vessel.

Further objects and features of the invention will be fully understood from the following detailed description with reference to the accompanying drawings, wherein:

DETAILED DESCRIPTION OF THE PREFERRED EMBODIMENTS

Figure 1:
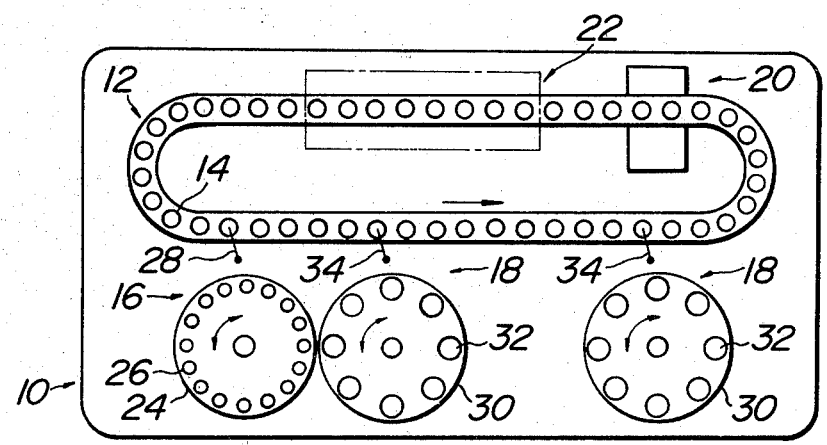
FIG. 1 is a diagrammatic view of one embodiment of an automatic analytical apparatus according to the invention.

FIG. 1 shows one embodiment of an automatic analytical apparatus according to the invention as a whole. In the present embodiment, an analytical apparatus 10 is provided with a single endless reaction line 12 along which is carried reaction vessels 14 step by step. Along the reaction line 12 are arranged a sample delivering station 16, a reagent delivering station 18, a photometric station 20 and a reaction vessel washing and drying station 22 in the order as mentioned.

The sample delivering station 16 is composed of a sample transfer mechanism 24 which preferably consists of a turntable rotatable in two directions and a sample delivering mechanism 28 operative to attract a given amount of sample from a sample vessel 26 disposed on the sample transfer mechanism 24 and deliver it into the reaction vessel 14. Similarly, the reagent delivering station 18 is composed of a reagent transfer mechanism 30 which preferably consists of a turntable rotatable in two directions and a reagent delivering mechanism 34 operative to attract a given amount of reagent from a reagent vessel 32 disposed on the reagent transfer mechanism 30 and deliver it into the reaction vessel 14. If desired, provision may be made of a plurality of reagent delivering stations 18.

The photometric station 20 is composed of a plurality of sets of light emitting elements and light receiving elements. The reaction vessel washing and drying station may be composed of any suitable well known washing and drying mechanism. If the reaction vessel is discarded without using it again, the reaction vessel washing and drying station may be replaced by a station that can discard the used reaction vessel and supply a new one.

Figure 2:
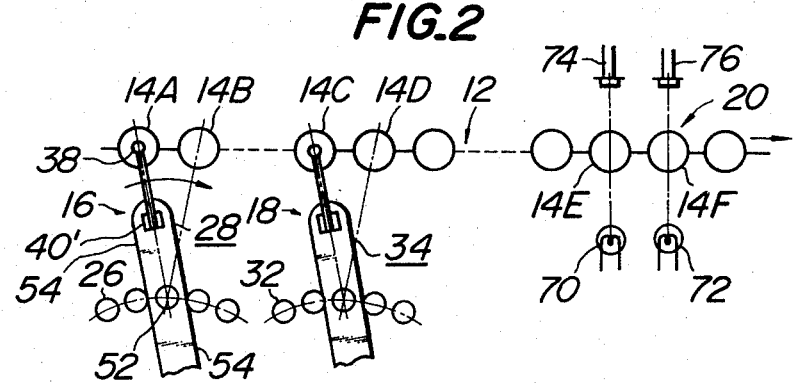
FIG. 2 is a diagrammatic view of essential parts of the apparatus shown in FIG. 1 in an enlarged scale.
Figure 3:
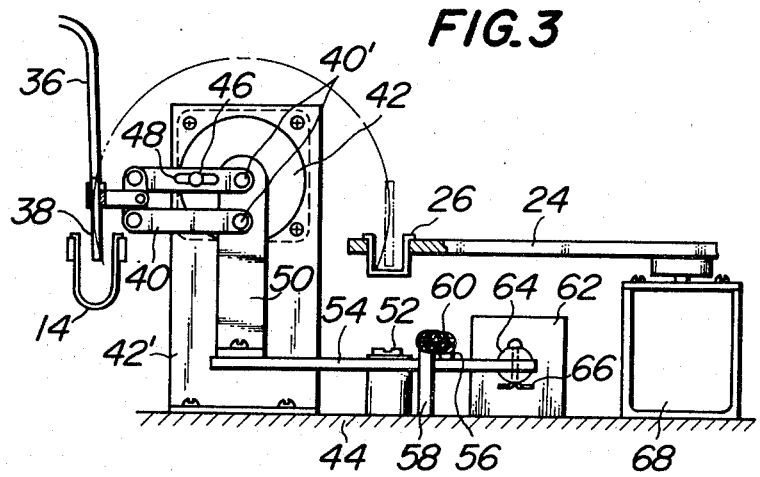
FIG. 3 is a side elevational view of a detailed construction of a delivering mechanism shown in FIGS. 1 and 2.

As shown in FIGS. 2 and 3, the sample delivering mechanism 28 of the sample delivering station 16 is provided with a sample delivering nozzle 38 connected through a flexible tube 36 to a pump (not shown). The sample delivering nozzle 38 is vertically held by a pantagraph mechanism 40 and adapted to be moved in parallel with a vertical plane. The pantagraph mechanism 40 is rotated by means of a pin 46 constituting an output member of a driving motor 42 and engaged with an elongate hole 48 formed in one of links of the pantagraph mechanism 40. The driving motor 42 is firmly fitted through a supporting member 42' to a base plate 44 of the apparatus 10. Another link of the pantagraph mechanism 40 extends downwardly and is secured to one end of a lever 54 rotatable about a vertical axis 52. The lever 54 is provided between the other end thereof and the supporting point thereof, i.e. the vertical axis 52 with a pin 56. The base plate 44 is provided at that portion thereof which is opposed to the pin 56 with a pin 58. Between these pins 56, 58 is interposed a coiled tension spring 60 which is normally operative to cause the lever 54 to rotate in a clockwise direction shown by an arrow in FIG. 2. To the other end of the lever 54 is connected a plunger 64 of a solenoid 62 through a pin 66, the solenoid 62 being operative to cause the lever 54 to move against the tensile force of the spring 60. The solenoid 62 is secured to the base plate 44.

As shown in FIG. 3, the sample transferring mechanism 24 is composed of a turntable adapted to be rotated by a reversible motor 68. When the pantagraph mechanism 40 is located at one of its terminal positions, the front end of the sample delivering nozzle 38 is positioned in the reaction vessel 14 on the reaction line 12, whereas when the pantagraph mechanism 40 is located at the other terminal position, the front end of the sample delivering nozzle 38 is positioned in the sample vessel 26 on the turntable 24. In this case, it is preferable to locate the sample delivering nozzle 38 and sample vessel 26 at a position above the vertical axis 52.

The concrete construction of the reagent delivering station 18 is the same as that of the above described sample delivering station 16 and hence is not described and not shown in the drawing.

As shown in FIG. 2, the photometric station 20 is provided with two sets of light emitting and light receiving elements 70, 74; 72, 76.

The automatic analytical apparatus constructed and arranged as above described will operate as follows. Before starting the analytical operation, the sample vessel 26 containing a sample to be analyzed is set on the sample transferring mechanism 24 and the reagent vessel 32 containing various kinds of reagents corresponding to the measurement items is set on the reagent transferring mechanism 30.

The sample transferring mechanism 24 functions to control the transferring operation thereof in response to a test body information. That is, the sample vessel 26 containing a specified sample is remained at its sample delivering position while a given amount of sample is delivered to each reaction vessel 14 which is the same in number as the measurement items required for the sample.

In the embodiment shown in the drawing, a set of two reaction vessels 14 are intermittently carried such that each reaction vessel 14 advances to every other position everytime the reaction line 12 is carried by one step. The sample delivering nozzle 38 is projected into the sample vessel 26 to attract a given amount of sample into the nozzle 38. Then, the motor 42 is energized to rotate the pantagraph mechanism 40 about its pivots 40', 40' to the position shown in FIG. 3 and move the sample delivering nozzle 38 in parallel with the vertical plane into the reaction vessel 14. At this position, the sample is supplied from the nozzle 38 into the reaction vessel 14.

As can be seen from FIGS. 2 and 3, after the sample has been delivered to one of the set of two reaction vessel 14A, the sample delivering nozzle 38 is returned to a new sample vessel 26 to attract the sample. Whereas, the solenoid 62 is energized to rotate the lever 54 about the vertical axis 52 against the force of the spring 60. In this case, the pantagraph mechanism 40 also is rotated about the vertical axis 52. Then, the motor 42 is energized again to displace the pantagraph mechanism 40 to the position shown in FIG. 3. As a result, the sample delivering nozzle 38 is moved in parallel with the vertical plane into the other reaction vessel 14B and then becomes operative to supply the sample thereinto.

In the sample delivering station 16, during the changeover of the delivering operation of the sample from the sample vessel 26 to the reaction vessel 14A to the delivering operation of the sample from the sample vessel 26 to the reaction vessel 14B, the reaction vessel is not carried. As a result, it is possible to deliver the sample from the sample vessel 26 into the two reaction vessels 14A, 14B during the unit carrying step of the reaction line 12.

If the solenoid 62 is energized to rotate the lever 54, pantagraph mechanism 40 and sample delivering nozzle 38 about the vertical axis 32, the output pin 46 of the motor 42 shown in FIG. 3 and engaged with the elongate hole 48 of the link of the pantagraph mechanism 40 is displaced in the lengthwise direction of the elongate hole 48. In other words, in order to allow the output pin 46 to displace in the lengthwise direction of the elongate hole 48, the output pin 46 is connected through the elongate hole 48 to the link of the pantagraph 40. The output pin 46 has a length which is sufficient to prevent the output pin 46 from detaching from the elongate hole 48 even when the pantagraph mechanism 40 is rotated about the vertical axis 52.

In the reagent delivering station 18, during the unit carrying step of the reaction vessel 14, the reagent corresponding to the measurement item is attracted from the reagent vessel 32 and delivered into one set of two reaction vessels 14C, 14D in the same manner as in the case of the sample delivering operation in the sample delivering station 16.

At a time when the required reagent delivered into the reaction vessel 14 reacts sufficiently with the sample to produce a test liquid, the test liquid thus obtained in the two reaction vessels 14E, 14F is subjected to the photometric operation independently from each other, that is, the test liquid in one of the reaction vessels 14E is subjected to the photometric operation by means of the light emitting element 70 and the light receiving element 74 and the test liquid in the other reaction vessel 14F is subjected to the photometric operation by means of the light emitting element 72 and the light receiving element 76 during the time corresponding to the unit carrying step, thereby obtaining the required measurement data.

Finally, the reaction vessel 14 subjected to the photometric operation is washed and dried at the washing and drying station 22 and then carried again to the sample delivering station 16.

As stated hereinbefore, the automatic analytical apparatus according to the invention is capable of delivering the sample and reagent to a plurality of reaction vessels by means of respective delivering mechanism during unit carrying step of the reaction vessel, respectively, and capable of effecting the photometric operation of the test liquid at a plurality of positions corresponding in number to the number of the reaction vessels delivered with the sample and the reagent. That is, let the time for the unit carrying step be T, the number of the reaction vessels be n and the sample or the reagent be delivered to n reaction vessels during the time T at the lapse of time of about T/n for each reaction vessel, the photometric operation can be effected for the time T at n position, respectively. As a result, it is possible to improve the treatment efficiency without shortening the time required for the photometric operation and hence always effect the photometric operation in a satisfactory precise manner.

The automatic analytical apparatus according to the invention has another advantage that since the delivering mechanism is displaceable to each of delivering positions corresponding to the plurality of reaction vessels it is not necessary to provide the delivering mechanism for each of the plurality of delivering positions, and as a result, the apparatus is simple in construction, reliable in operation and less expensive.

In the embodiment described above, a set of two reaction vessels are carried, the sample and reagent are delivered to these two reaction vessels, respectively, and the photometric operations with respect to these two reaction vessels are effected at the same time. But, the invention is not limited to such embodiment only. For example, if the reaction line is arranged along the arcuate moving course of the pantagraph mechanism operative to rotate about the vertical axis shown in FIG. 3, the sample and reagent may be delivered to the reaction vessels located at a plurality of positions more than 3 during the unit carrying step. In this case, more than 3 of the photometric optical systems are separated from each other and arranged in the moving direction of the reaction line.

What is claimed is:

1. In an automatic analytical apparatus comprising a single reaction line, reaction vessels arranged along the reaction line and operative to be carried in a stepwise manner, a sample delivering station for delivering a sample into the reaction vessel during an interval between successive carrying steps, a reagent delivering station for delivering a reagent corresponding to a measurement item into the reaction vessel to form a test liquid during the interval between the successive carrying steps, and a photometering station for subjecting the test liquid to a photometric operation, the improvement comprising:
    (a) sample and reagent delivering means for delivering at least one kind of sample and at least one kind of reagent into respective reaction vessels of a group consisting of a plurality of successive reaction vessels during an interval between successive carrying steps during each of which said group of the plurality of reaction vessels are carried along said single reaction line, and
    (b) means comprising the plurality of photometers arranged along said single reaction line for photometering the test liquids contained in said plurality of the successive reaction vessels at the same time during said interval between the successive carrying steps.

2. The apparatus according to claim 1, wherein
    (a) said sample and reagent delivering means is composed of a sample delivering mechanism and a reagent delivering mechanism, each mechanism including a delivering nozzle, and
    (b) the delivering nozzle is operative to move between the sample or reagent vessel and the reaction vessel and deliver the sample or reagent into selected one of a plurality of reaction vessels on the reaction line.

3. The apparatus according to claim 2 and further comprising means for moving a desirous sample or reagent vessel to a position where the delivering nozzle can be located.

4. The apparatus according to claim 2 or 3 and further comprising
    (a) a pantagraph mechanism for moving the delivering nozzle in parallel with a vertical plane, and
    (b) means for rotating a support member for said pantagraph in horizontal plane about a vertical axis, whereby
    (c) the delivering nozzle brought into one of terminal positions of the pantagraph mechanism and a desirous sample vessel and reagent vessel are located at a position above said vertical axis and
    (d) a plurality of reaction vessels adapted to be delivered with the desirous sample or reagent are arranged along an arcuate course which is traced by the delivering nozzle at the other terminal position of the pantagraph mechanism when it is rotated about said vertical axis.

* * * * *